(12) United States Patent
Sakai

(10) Patent No.: US 11,822,068 B2
(45) Date of Patent: Nov. 21, 2023

(54) INSERTION INSTRUMENT

(71) Applicant: OLYMPUS CORPORATION, Tokyo (JP)

(72) Inventor: Seiji Sakai, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 576 days.

(21) Appl. No.: 17/132,414

(22) Filed: Dec. 23, 2020

(65) Prior Publication Data
US 2021/0109311 A1 Apr. 15, 2021

Related U.S. Application Data

(63) Continuation of application No. PCT/JP2019/005365, filed on Feb. 14, 2019.

(30) Foreign Application Priority Data

Jul. 6, 2018 (JP) .................................. 2018-129399

(51) Int. Cl.
*G02B 23/24* (2006.01)
*A61B 1/00* (2006.01)
(Continued)

(52) U.S. Cl.
CPC .......... *G02B 23/2476* (2013.01); *A61B 1/009* (2022.02); *A61B 1/0011* (2013.01);
(Continued)

(58) Field of Classification Search
CPC .... G02B 23/2476; G02B 23/243; G02B 7/04; A61B 1/009; A61B 1/0011; A61B 1/00128; A61B 1/00188
(Continued)

(56) References Cited

U.S. PATENT DOCUMENTS 5,531,664 A * 7/1996 Adachi ................ A61B 1/0052
600/152
5,908,381 A * 6/1999 Aznoian ................ A61B 10/06
606/205
(Continued)

FOREIGN PATENT DOCUMENTS

EP 2074926 A2 7/2009
EP 2581028 A1 4/2013
(Continued)

OTHER PUBLICATIONS

International Search Report dated Apr. 23, 2019 issued in PCT/JP2019/005365.

*Primary Examiner* — William R Alexander
*Assistant Examiner* — Sharrief I Broome
(74) *Attorney, Agent, or Firm* — Scully, Scott, Murphy & Presser, P.C.

(57) ABSTRACT

An endoscope has a configuration in which a wire guide tube is configured as a tube consecutively formed of polyetheretherketone from one end side to another end side, an opening penetrating is provided in a radial direction at part of a wall portion of a second coupling member into which an end part of the wire guide tube is inserted, a concave portion corresponding to the opening is provided at an outer peripheral surface of the end part of the wire guide tube, and a bonding agent integrally fills the opening and the concave portion to connect the wire guide tube and a coupling portion (the second coupling member).

10 Claims, 13 Drawing Sheets

(51) Int. Cl.
  *G02B 7/04* (2021.01)
  *A61B 1/005* (2006.01)
(52) U.S. Cl.
  CPC ...... *A61B 1/00128* (2013.01); *A61B 1/00188* (2013.01); *G02B 7/04* (2013.01); *G02B 23/243* (2013.01)
(58) Field of Classification Search
  USPC ........................................... 359/822
  See application file for complete search history.

(56) References Cited

U.S. PATENT DOCUMENTS

| | | | |
|---|---|---|---|
| 6,117,071 A * | 9/2000 | Ito | A61B 1/05 600/129 |
| 6,712,817 B1 * | 3/2004 | Goto | A61B 18/1485 606/47 |
| 2009/0171158 A1 | 7/2009 | Matsuo et al. | |
| 2009/0185032 A1 * | 7/2009 | Sakai | F03G 7/065 359/813 |
| 2012/0220828 A1 | 8/2012 | Iwasaki | |
| 2016/0135795 A1 * | 5/2016 | Eto | A61B 1/018 600/566 |
| 2016/0338771 A1 * | 11/2016 | Kobayashi | A61B 18/1492 |
| 2017/0139198 A1 | 5/2017 | Kibayashi | |
| 2023/0235767 A1 * | 7/2023 | Hirasawa | F16B 9/09 403/382 |

FOREIGN PATENT DOCUMENTS

| | | |
|---|---|---|
| JP | 2000-237202 A | 9/2000 |
| JP | 2008-110503 A | 5/2008 |
| JP | 2009-153714 A | 7/2009 |
| JP | 2009-300761 A | 12/2009 |
| JP | 2013-188343 A | 9/2013 |
| JP | 2015-58118 A | 3/2015 |
| JP | 2017-072657 A | 4/2017 |
| WO | WO 2012/063816 A1 | 5/2012 |
| WO | WO 2016/060081 A1 | 4/2016 |

* cited by examiner

INSERTION INSTRUMENT

CROSS REFERENCE TO RELATED APPLICATION

This application is a continuation application of PCT/JP2019/005365 filed on Feb. 14, 2019 and claims benefit of Japanese Application No. 2018-129399 filed in Japan on Jul. 6, 2018, the entire contents of which are incorporated herein by this reference.

BACKGROUND OF THE INVENTION

1. Field of the Invention

The present invention relates to an insertion instrument in which a movement lens of an observation optical system provided at a distal end portion is moved forward and backward by an operation wire.

2. Description of the Related Art

In recent years, endoscopes have been widely used in the medical and industrial fields. The endoscope includes an observation optical system unit at a distal end portion of an elongated insertion portion, and allows a user to observe inside a pipe line by inserting the insertion portion into the pipe line.

Among endoscopes of this kind, what is called a zoom endoscope is known in which at least one lens in a lens group included in an objective optical system unit is a movement lens movable in the direction of the optical axis to allow change of optical properties such as a focal depth, an imaging magnification, and a view angle for an observation site.

For example, International Publication No. WO2016/060081 discloses an endoscope including: a distal end rigid portion; an objective lens fixed barrel disposed in a through-hole of the distal end rigid portion; a moving frame (driven body) that is disposed at a holding frame provided continuously with the objective lens fixed barrel and holds the movement lens; a wire unit (operation wire) having one end side coupled with a wire unit coupling convex portion provided to the moving frame and the other end side coupled with an operation lever provided to an operation portion; and a wire guide member (wire guide tube and stainless steel pipe) covering the wire unit, and the optical properties of the objective optical system unit can be changed as the wire unit moves the moving frame forward and backward in the direction of the optical axis in cooperation with the operation lever.

In International Publication No. WO2016/060081 described above, the wire guide member includes a wire guide tube, and a net pipe covering the outer periphery of the wire guide tube. In this case, the wire guide tube is requested to have a small slide resistance with the operation wire, and in addition, flexibility that allows bending following a bending portion of the insertion portion. Thus, for example, a PTFE (polytetrafluoroethylene (tetrafluoro)) tube is typically excellently used as the wire guide tube. The net pipe is provided to reduce extension of the wire guide tube and ensure operability of the moving frame by the wire unit when the wire guide tube is configured as a flexible PTFE tube, and the net pipe is formed by weaving a stainless steel thin wire or the like.

SUMMARY OF THE INVENTION

An insertion instrument according to an aspect of the present invention includes: a wire having one end part fixed to a driven body and configured to transfer drive power from a drive source to the driven body; a tube that is consecutively formed of polyetheretherketone from one end side to another end side and into which the wire is inserted; a first coupling member fixed to an objective unit in which the driven body is incorporated; a second coupling member fixed to the first coupling member, the second coupling member including a tubular portion into which an end part of the tube is inserted, the second coupling member being configured to couple the tube; an opening penetrating in a radial direction at part of a wall portion of the second coupling member; a concave portion formed at an outer peripheral surface of the tube so as to correspond to the opening; and a bonding agent integrally filling the opening and the concave portion.

An insertion instrument according to another aspect of the present invention includes: a wire having one end part fixed to a driven body and configured to transfer drive power from a drive source to the driven body; a tube that is consecutively formed of polyetheretherketone from one end side to another end side and into which the wire is inserted; a first coupling member fixed to an objective unit in which the driven body is incorporated; a second coupling member fixed to the first coupling member, the second coupling member including a tubular portion into which an end part of the tube is inserted, the second coupling member being configured to couple the tube; and a plastic deformation portion provided to the second coupling member, and the end part of the tube is fixed by swaging that plastically deforms the plastic deformation portion inward in a radial direction of the second coupling member.

DETAILED DESCRIPTION OF THE PREFERRED EMBODIMENTS

Figure 1:
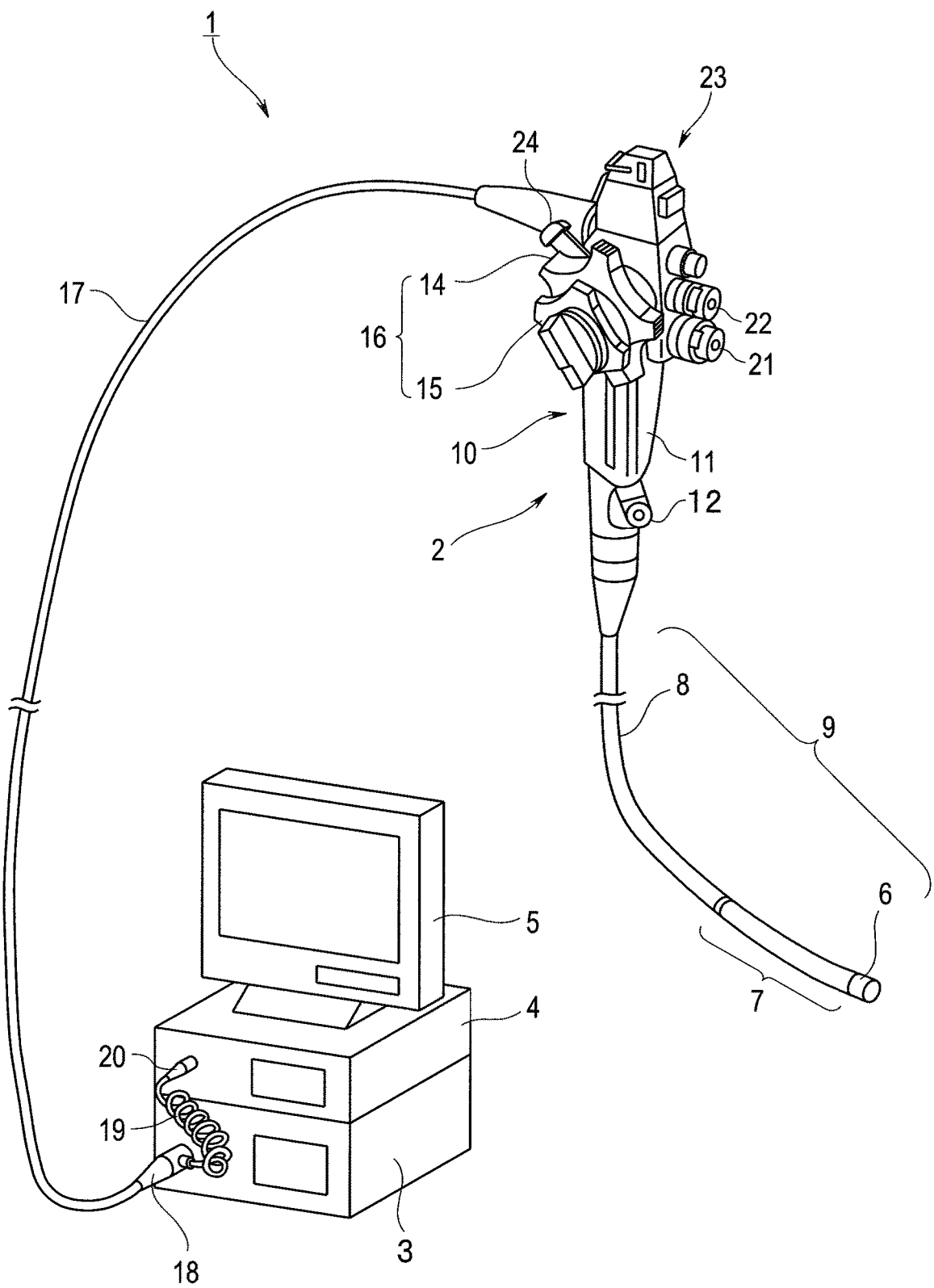
FIG. 1 is an explanatory diagram illustrating the entire configuration of an endoscope according to a first embodiment.
Figure 2:
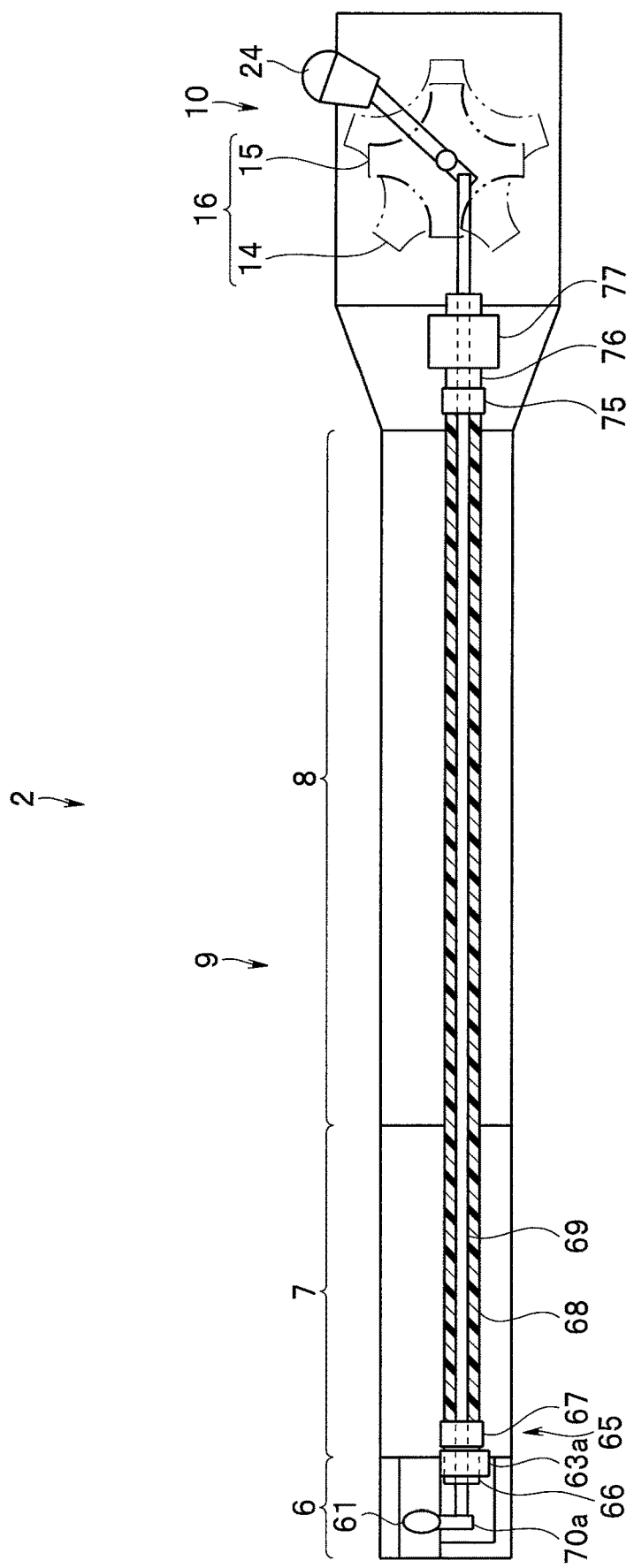
FIG. 2 is a schematic diagram illustrating a lens drive mechanism of the endoscope according to the first embodiment.
Figure 3:
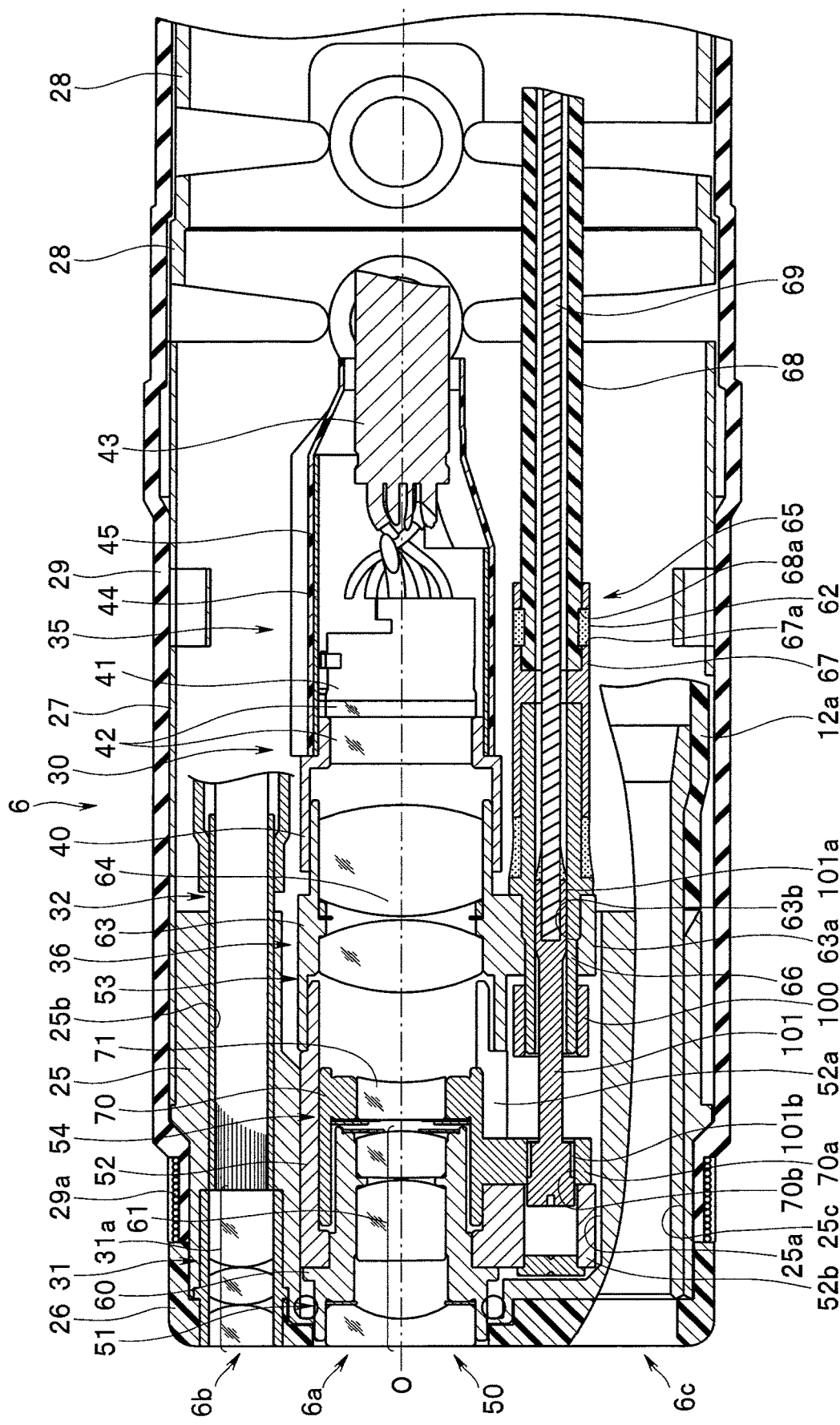
FIG. 3 is a main part cross-sectional view of a distal end portion according to the first embodiment.
Figure 4:
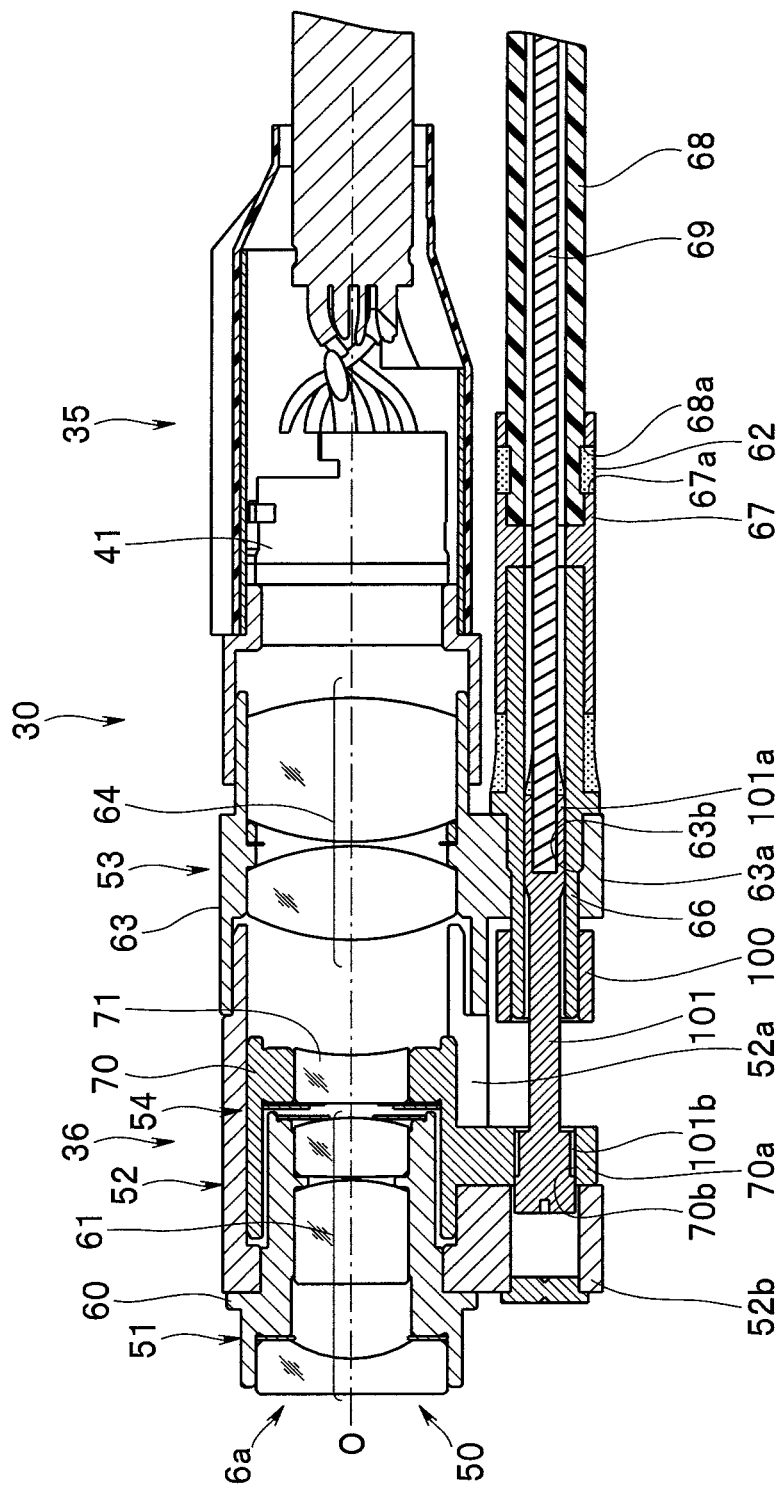
FIG. 4 is a main part cross-sectional view when an observation optical system is in a wide state according to the first embodiment.
Figure 5:
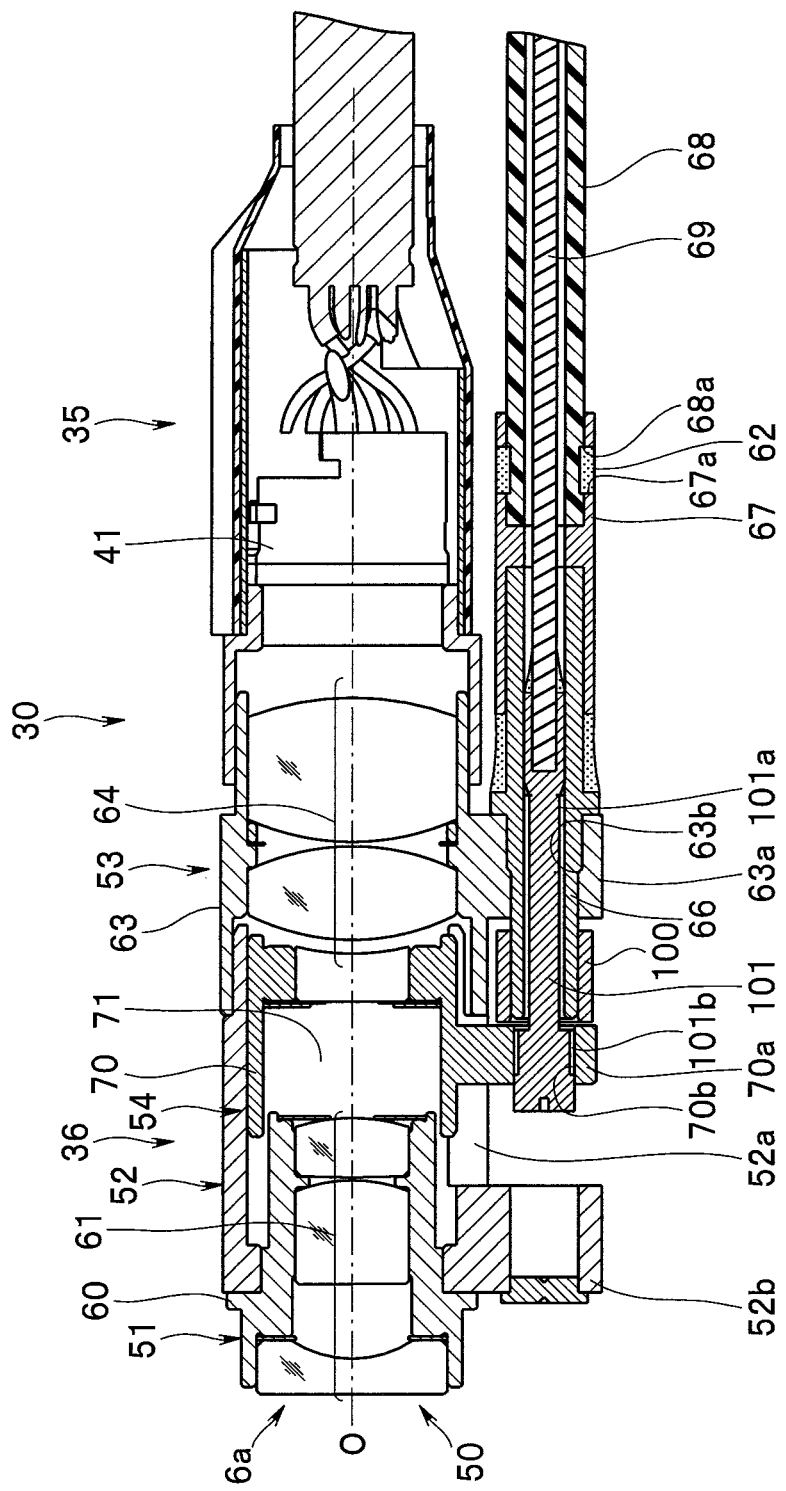
FIG. 5 is a main part cross-sectional view when the observation optical system is in a telephoto state according to the first embodiment.
Figure 6:
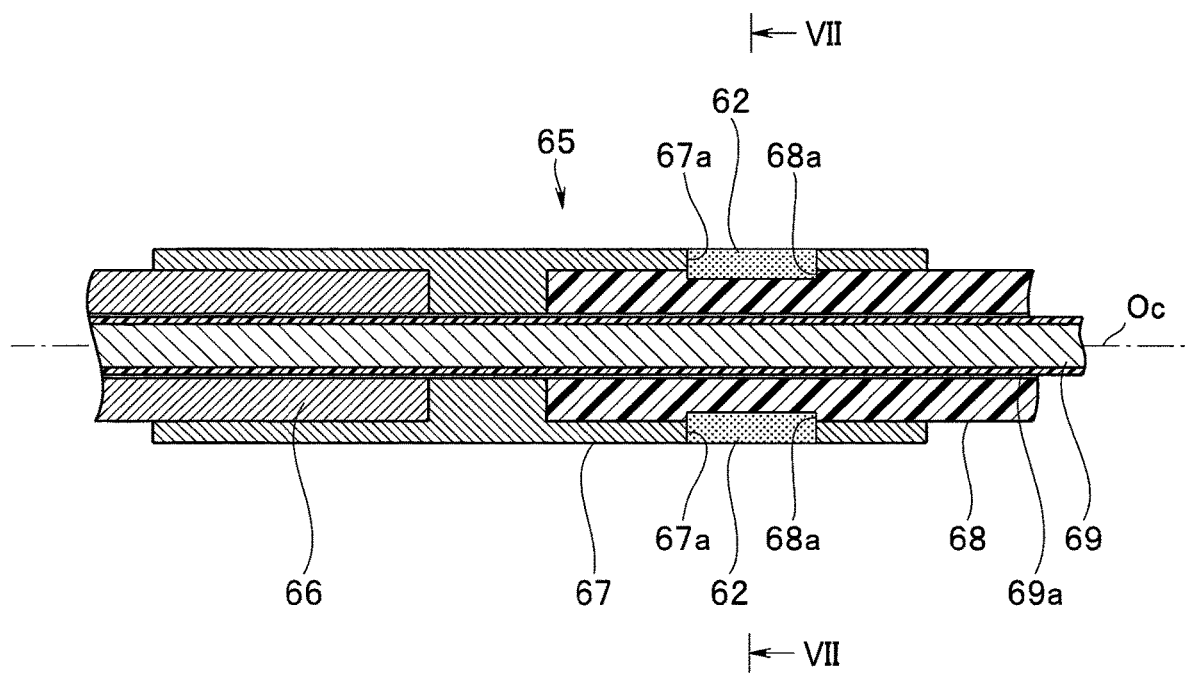
FIG. 6 is a main part cross-sectional view illustrating a connection structure of a distal end side of a wire guide tube and a coupling portion according to the first embodiment.
Figure 7:
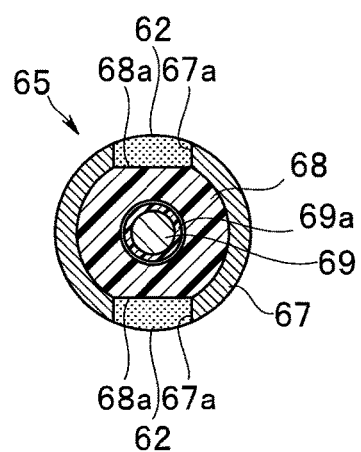
FIG. 7 is a cross-sectional view taken along line VII-VII in FIG. 6 according to the first embodiment.
Figure 8:
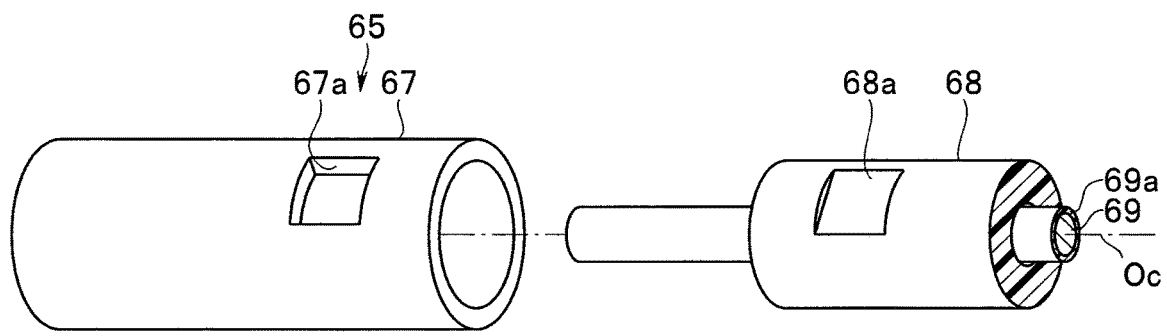
FIG. 8 is an exploded perspective view illustrating the wire guide tube and the coupling portion according to the first embodiment.
Figure 9:
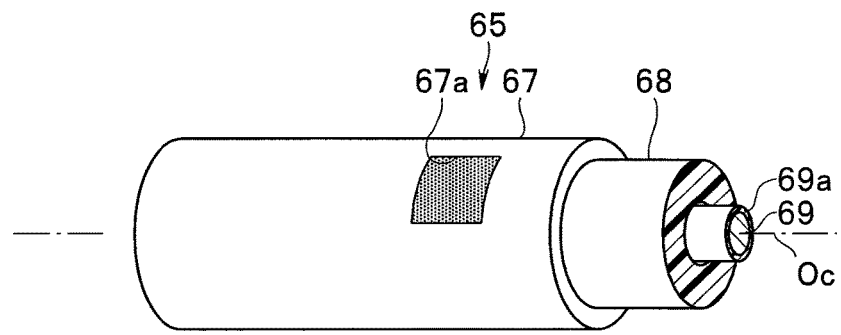
FIG. 9 is a perspective view illustrating the wire guide tube connected with the coupling portion according to the first embodiment.
Figure 10:
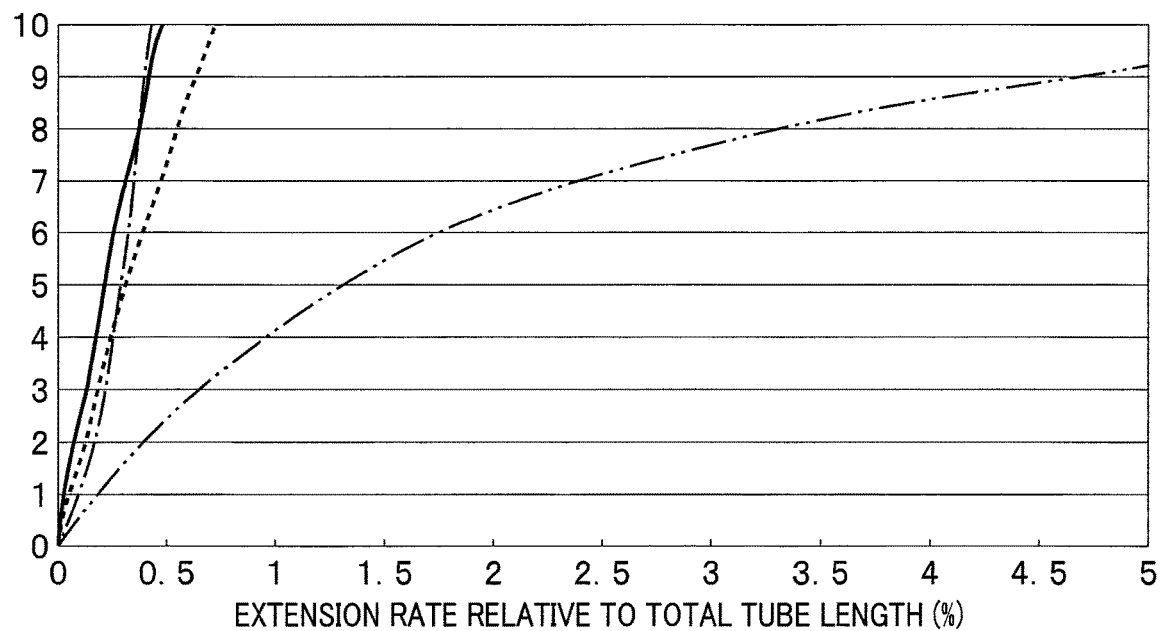
FIG. 10 is a characteristic diagram illustrating the relation between pulling force of each material and an extension rate relative to a total tube length according to the first embodiment.

Embodiments of the present invention will be described below with reference to the accompanying drawings. The drawings relate to a first embodiment of the present invention: FIG. 1 is an explanatory diagram illustrating the entire configuration of an endoscope; FIG. 2 is a schematic diagram illustrating a lens drive mechanism of the endoscope; FIG. 3 is a main part cross-sectional view of a distal end portion; FIG. 4 is a main part cross-sectional view when an observation optical system is in a wide state; FIG. 5 is a main part cross-sectional view when the observation optical system is in a telephoto state; FIG. 6 is a main part cross-sectional view illustrating a connection structure of a distal end side of a wire guide tube and a coupling portion; FIG. 7 is a cross-sectional view taken along line VII-VII in FIG. 6;

FIG. 8 is an exploded perspective view illustrating the wire guide tube and the coupling portion; FIG. 9 is a perspective view illustrating the wire guide tube connected with the coupling portion; and FIG. 10 is a characteristic diagram illustrating the relation between pulling force of each material and an extension rate relative to a total tube length.

As illustrated in FIG. 1, an electronic endoscope system (hereinafter simply referred to as an endoscope system) 1 as an insertion system of the present embodiment includes an electronic endoscope apparatus (hereinafter simply referred to as an endoscope) 2 that is an endoscope as an exemplary insertion instrument, a light source device 3, a video processor 4, and a color monitor 5, which are electrically connected with one another.

The endoscope 2 includes an insertion portion 9, and an operation portion 10 from which the insertion portion 9 is extended, and a universal cord 17 extending from the operation portion 10 is connected with the light source device 3 through a scope connector 18.

A scope cable 19 in a coil shape is extended from the scope connector 18. An electrical connector portion 20 is provided on the other end side of the scope connector 18 and connected with the video processor 4.

The insertion portion 9 has a configuration in which a distal end portion 6, a bending portion 7, and a flexible tube portion 8 are provided continuously and sequentially from a distal end side.

As illustrated in, for example, FIG. 3, an observation window 6a, an illumination window 6b, and a suction opening 6c serving as a treatment instrument introduction port are disposed at a distal end surface of the distal end portion 6. In addition, an observation window cleaning nozzle and a forward water feeding port (not illustrated) are disposed at the distal end surface of the distal end portion 6. Note that, in the present embodiment, up, down, right, and left directions of the endoscope 2 are defined, for example, in association with up, down, right, and left directions of an endoscope image observed through the observation window 6a.

As illustrated in FIG. 1, the operation portion 10 includes an operation portion body 11 included in a grasping portion, a forceps port 12 disposed on the distal end side of the operation portion body 11, a bending operation portion 16 constituted by two bending operation knobs 14 and 15 provided on a proximal end side of the operation portion body 11, an air/water feeding control portion 21, a suction control portion 22, a plurality of switch portions 23 mainly for operating an image pickup function, and an operation lever 24 for operating, for example, a focusing function or a zooming function of performing magnification adjustment to, for example, wide and telephoto states by moving forward and backward a movement lens provided in an image pickup unit to be described later.

Next, a detailed configuration of the distal end portion 6 of the endoscope 2 will be mainly described. As illustrated in FIG. 3, the distal end portion 6 includes a distal end rigid member 25 having a substantially cylindrical shape. A distal end cover 26 forming the distal end surface of the distal end portion 6 is bonded and fixed on the distal end side of the distal end rigid member 25.

A plurality of bending pieces 28 included in the bending portion 7 are provided continuously through a distal end frame 27 on the proximal end side of the distal end rigid member 25. The outer peripheries of the distal end rigid member 25, the distal end frame 27, and the bending pieces 28 are integrally covered by an external skin 29. A distal end outer peripheral portion of the external skin 29 is fixed to the distal end rigid member 25 by a reel bonding portion 29a.

An image pickup unit holding hole 25a is provided to the distal end rigid member 25 at a position corresponding to the observation window 6a. An image pickup unit 30 is disposed by fitting and insertion in the image pickup unit holding hole 25a and fixed by a set screw (not illustrated). The distal end of the image pickup unit 30 is exposed outside the distal end cover 26 to form the observation window 6a at the distal end portion 6.

An illumination unit holding hole 25b is provided to the distal end rigid member 25 at a position corresponding to the illumination window 6b. An illumination unit 31 is disposed by fitting and insertion in the illumination unit holding hole 25b. The distal end of an illumination optical system 31a provided in the illumination unit 31 is exposed outside the distal end cover 26 to form the illumination window 6b at the distal end portion 6.

The illumination unit 31 of the present embodiment irradiates a subject with light supplied from the light source device 3 through a light guide bundle 32 as a light source. Thus, the distal end side of the light guide bundle 32 is held in the illumination unit holding hole 25b on the proximal end side of the illumination unit 31. The proximal end side of the light guide bundle 32 is inserted from the insertion portion 9 into the universal cord 17 through the operation portion 10 so that illumination light from the light source device 3 can be transmitted to the illumination window 6b when the scope connector 18 is connected with the light source device 3.

A through-hole 25c for forming the suction opening 6c at the distal end portion 6 is provided at the distal end rigid member 25. The through-hole 25c communicates with the forceps port 12 of the operation portion 10 mainly through a treatment instrument channel 12a inserted and disposed in the insertion portion 9.

The following describes a detailed configuration of the image pickup unit 30 with reference to, for example, FIGS. 3 to 5.

As illustrated in FIG. 3, the image pickup unit 30 of the present embodiment includes a solid image pickup unit 35, and an observation optical system unit 36 continuously provided on the distal end side of the solid image pickup unit 35.

The solid image pickup unit 35 includes a solid image pickup device holding frame 40, and a front surface side of a solid image pickup device 41 that is an image pickup device such as a CCD or a CMOS is held at the solid image pickup device holding frame 40 through an optical member 42 such as a cover glass. A plurality of communication lines branching from a cable 43 are electrically connected with the solid image pickup device 41 through an FPC or the like (not illustrated). The cable 43 is inserted and disposed inside the endoscope 2 and electrically connected with the video processor 4 through the electrical connector portion 20.

A reinforcement frame 44 is continuously provided on an outer peripheral portion of the solid image pickup device holding frame 40 on the proximal end side, and a thermal contraction tube 45 covering up to a distal end part of the cable 43 is provided on the outer periphery of the reinforcement frame 44.

The observation optical system unit 36 of the present embodiment includes an observation optical system 50 of a focal point switching scheme, which achieves the focusing function or the zooming function by moving forward and backward an internal lens to change the optical property (focal length).

More specifically, the observation optical system unit 36 includes a front group lens unit 51 positioned on the distal end side, a coupling frame 52 continuously provided on the proximal end side of the front group lens unit 51, a rear group lens unit 53 coupled with the front group lens unit 51 through the coupling frame 52, and a movement lens unit 54 capable of moving forward and backward inside the coupling frame 52 in the direction of a photographing optical axis O.

The front group lens unit 51 includes a front group lens frame 60 as a fixed barrel, and front group lenses 61 including a plurality of fixed lenses held at the front group lens frame 60.

The coupling frame 52 is configured as a member having a substantially cylindrical shape. The coupling frame 52 is provided with a slit 52a extending in a direction same as the direction of the photographing optical axis O. The proximal end side of the slit 52a is opened at the proximal end of the coupling frame 52. A wide state positioning portion 52b protruding in the outward radial direction of the coupling frame 52 is provided on the distal end side of the coupling frame 52 and blocks the distal end side of the slit 52a.

The rear group lens unit 53 includes a rear group lens frame 63 that is a fixed barrel having a distal end side coupled with the front group lens frame 60 through the coupling frame 52, and rear group lenses 64 including a plurality of fixed lenses held at the rear group lens frame 63.

A wire support portion 63a protruding in the outward radial direction of the rear group lens frame 63 is provided to the rear group lens frame 63. The wire support portion 63a is positioned to squarely face the wide state positioning portion 52b when the rear group lens frame 63 is coupled with the front group lens frame 60 through the coupling frame 52. The wire support portion 63a is provided with a screw hole 63b penetrating in the direction of the optical axis O.

A first coupling member 66 having a hollow male screw shape is screwed into the screw hole 63b. A telephoto state positioning member 100 is screwed into a screw part of the first coupling member 66, and a protrusion amount of the telephoto state positioning member 100 in an axial direction is adjusted to perform positioning in the telephoto state.

A proximal end side outer peripheral portion of the first coupling member 66 and a distal end inner peripheral portion of a second coupling member 67 are engaged with each other, and the distal end of a wire guide tube 68 is inserted into and connected with the inner periphery of a proximal end portion of the second coupling member 67.

An operation wire 69 as a wire made of, for example, a stainless steel wire is inserted into the wire guide tube 68 to be able to move forward and backward, and the distal end side of the operation wire 69 protrudes from the telephoto state positioning member 100.

As illustrated in FIG. 2, an end part of the wire guide tube 68 on the proximal end side is inserted into and connected with a distal end portion inner periphery of a third coupling member 75. A stainless steel pipe 76 is inserted into and connected with a proximal end inner periphery of the third coupling member 75. The third coupling member 75 is fixed to a fixation portion 77 provided in the operation portion 10. The proximal end side of the operation wire 69 protrudes from the stainless steel pipe 76 and is coupled with the operation lever 24 as a drive source. Accordingly, the operation wire 69 moves forward and backward inside the wire guide tube 68 in accordance with a swinging state of the operation lever 24.

The movement lens unit 54 includes a movement lens frame 70 as a moving frame (driven body) that is movable in the coupling frame 52, and a movement lens 71 held at the movement lens frame 70.

An operation rod 70a protruding in the outward radial direction of the movement lens frame 70 is provided to the movement lens frame 70. The operation rod 70a protrudes outside the coupling frame 52 through the slit 52a and faces the wide state positioning portion 52b and the telephoto state positioning member 100. A screw hole 70b penetrating in the direction of the photographing optical axis O is provided to the operation rod 70a, and an operation wire coupling member 101 provided with a screw part 101b at the distal end and provided with a connection hole 101a into and with which the operation wire 69 is inserted and connected at the proximal end is screwed into and connected with the screw hole 70b.

Accordingly, in cooperation with an operation on the operation lever 24, the movement lens unit 54 can move forward and backward along the photographing optical axis O between, for example, a wide position (refer to FIG. 4) at which the operation rod 70a contacts the wide state positioning portion 52b and a telephoto position (refer to FIG. 5) at which the operation rod 70a contacts the telephoto state positioning member 100.

In the endoscope 2 having the above-described configuration, the wire guide tube 68 is configured as a single tube made of polyetheretherketone (PEEK) over the entire range from the distal end to the proximal end.

PEEK is a material that is excellent in a fatigue characteristic, an impact characteristic, and the like and also has a chemical-resistant characteristic. In addition, PEEK is also a material that is excellent in a pulling characteristic. For example, as illustrated in FIG. 10, a PEEK tube (illustrated with a solid line in FIG. 10) has a significantly small extension rate (%) relative to the total tube length against pulling force (N) as compared to a PTFE tube having an equivalent shape (illustrated with a dashed and double-dotted line in FIG. 10). Note that the extension rate can have characteristics equivalent to, for example, those of an extension rate when the outer periphery of the PTFE tube is covered by a net pipe made of stainless steel thin wires (illustrated with a dashed and single-dotted line in FIG. 10).

However, PEEK has a low affinity with a bonding agent, and thus it is difficult to ensure a sufficient bonding strength by simply bonding the wire guide tube 68 made of a PEEK tube to a tubular portion 67 by using a bonding agent.

To increase the bonding strength, a concave portion 68a is formed at a distal end portion of the wire guide tube 68 of the present embodiment as illustrated in, for example, FIGS. 6 to 9. The concave portion 68a is formed by, for example, cutting out part of an outer peripheral portion of the wire guide tube 68 into a flat plate shape having a predetermined width in a direction orthogonal to the direction of a central axis Oc of the wire guide tube 68.

An opening 67a penetrating through a wall portion of the second coupling member 67 is formed in the second coupling member 67 at a position corresponding to the concave portion 68a.

After the wire guide tube 68 is inserted into the second coupling member 67, a bonding agent 62 such as resin integrally fills the opening 67a and the concave portion 68a to solidly connect the wire guide tube 68 with the second coupling member 67 by bonding.

Note that although detailed description is omitted, the operation portion 10 is connected with an end part (end part on the proximal end side) of the wire guide tube 68 through a configuration similar to that of a coupling portion 65.

In the present embodiment in which the wire guide tube 68 is configured as a PEEK tube as described above, a layer 69a made of PTFE (polytetrafluoroethylene) or the like is desirably formed on the surface of the operation wire 69 to reduce slide resistance of the operation wire 69.

To prevent damage due to interference with other internal components (the treatment instrument channel 12a, the light guide bundle 32, the cable 43, and the like) inserted inside the insertion portion 9, the hardness of the wire guide tube 68 is desirably set to be between the highest hardness and the lowest hardness of the other internal components. The hardness adjustment can be performed by, for example, optimizing the thickness of the wire guide tube 68 or the like.

According to such an embodiment, the endoscope 2 having excellent durability with a simple configuration and capable of accurately operating the movement lens frame 70 through the operation wire 69 can be achieved by configuring the wire guide tube 68 as a tube consecutively formed of polyetheretherketone from one end side (the distal end side) to the other end side (the proximal end side), providing the opening 67a penetrating in the radial direction to part of the wall portion of the first coupling member 67 into which the end part of the wire guide tube 68 is inserted, providing the concave portion 68a corresponding to the opening 67a to the outer peripheral surface of the end part of the wire guide tube 68, and integrally filling the opening 67a and the concave portion 68a with the bonding agent 62 to connect the wire guide tube 68 and the coupling portion 65 (tubular portion 67).

Specifically, since the wire guide tube 68 is consecutively formed of polyetheretherketone from one end side (the distal end side) to the other end side (the proximal end side), it is possible to maintain the length of the wire guide tube at an appropriate length and accurately operate the movement lens frame 70 through the operation wire 69 even when bending or the like is repeated at the bending portion 7 or the flexible tube portion 8.

Since the opening 67a penetrating in the radial direction is provided at part of the wall portion of the first coupling member 67 into which the end part of the wire guide tube 68 is inserted, the concave portion 68a corresponding to the opening 67a is provided at the outer peripheral surface of the end part of the wire guide tube 68, and the bonding agent 62 integrally fills the opening 67a and the concave portion 68a to connect the wire guide tube 68 and the coupling portion 65 (tubular portion 67), it is possible to achieve excellent durability with a simple configuration even when the wire guide tube 68 having a low affinity with a bonding agent and having an extremely small diameter is connected with the coupling portion 65.

Figure 11:
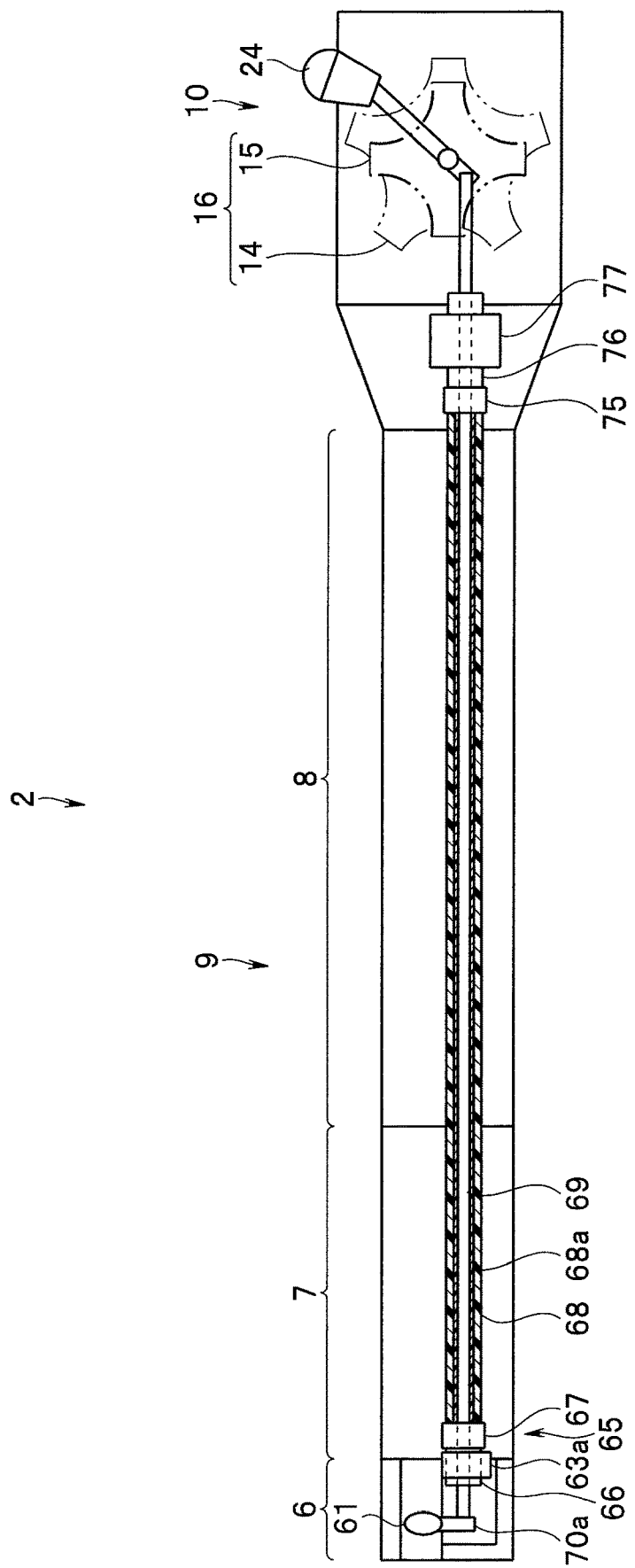
FIG. 11 is a schematic diagram illustrating the lens drive mechanism of the endoscope according to a first modification of the first embodiment.

Although the embodiment describes above an exemplary configuration in which the layer 69a made of PTFE (polytetrafluoroethylene) or the like is formed on the surface of the operation wire 69, a layer 68a made of PTFE (polytetrafluoroethylene) or the like may be formed on the inner surface of the wire guide tube 68 in place of the surface of the operation wire 69 as illustrated in, for example, FIG. 11. Note that, in this case, the wire guide tube 68 needs to be formed at a small thickness since the layer 68a is formed, but in such a case as well, it is possible to maintain a sufficiently small extension rate relative to the total tube length against pulling force as illustrated with, for example, a dashed line in FIG. 10.

Figure 12:
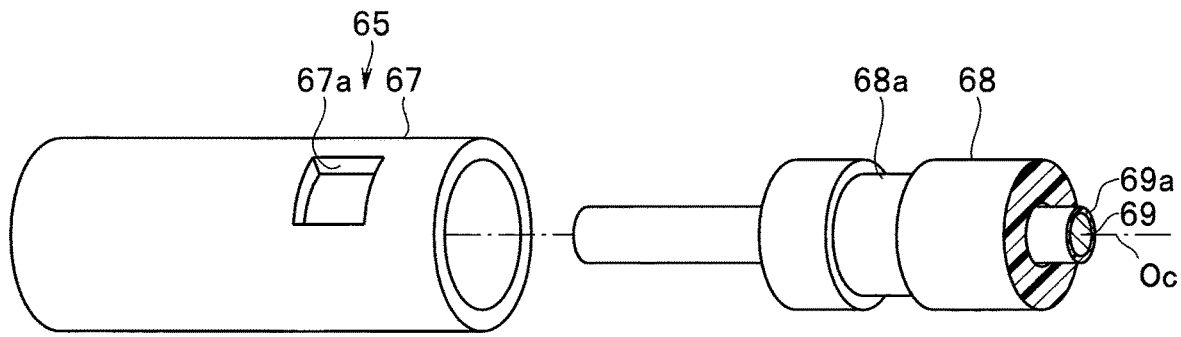
FIG. 12 is an exploded perspective view illustrating the wire guide tube and the coupling portion according to a second modification of the first embodiment.
Figure 13:
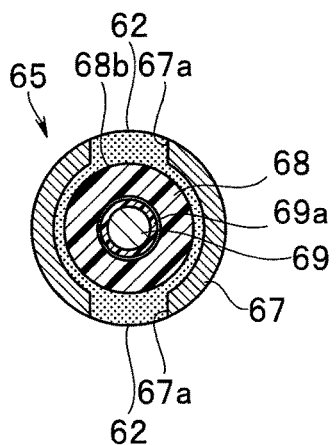
FIG. 13 is a main part cross-sectional view illustrating the connection structure of the distal end side of the wire guide tube and the coupling portion according to the second modification of the first embodiment.

In place of the concave portion 68a obtained by cutting out part of the outer peripheral portion of the wire guide tube 68 into a flat plate shape, a concave portion 68b may be formed by cutting out part of the outer peripheral portion of the wire guide tube 68 into an annular shape about the central axis Oc as illustrated in, for example, FIGS. 12 and 13.

With this configuration, it is easy to fabricate the concave portion 68b and position the concave portion 68b with respect to the opening 67a of the second coupling member 67.

Figure 14:
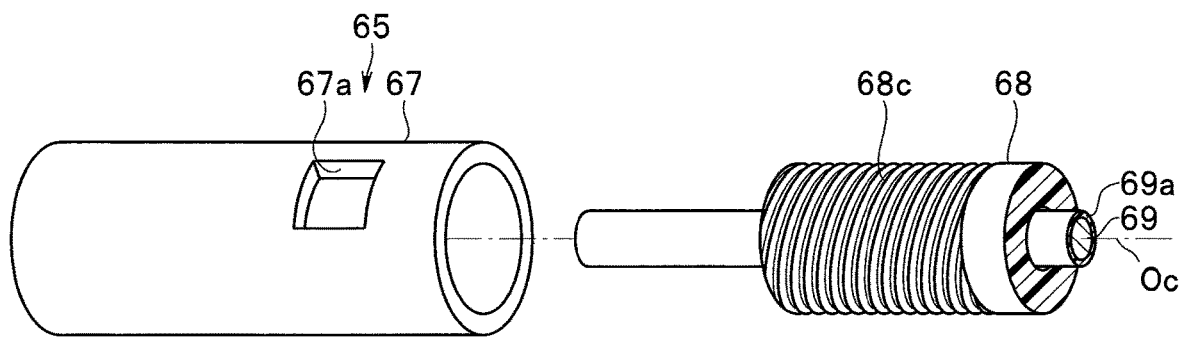
FIG. 14 is an exploded perspective view illustrating the wire guide tube and the coupling portion according to a third modification of the first embodiment.
Figure 15:
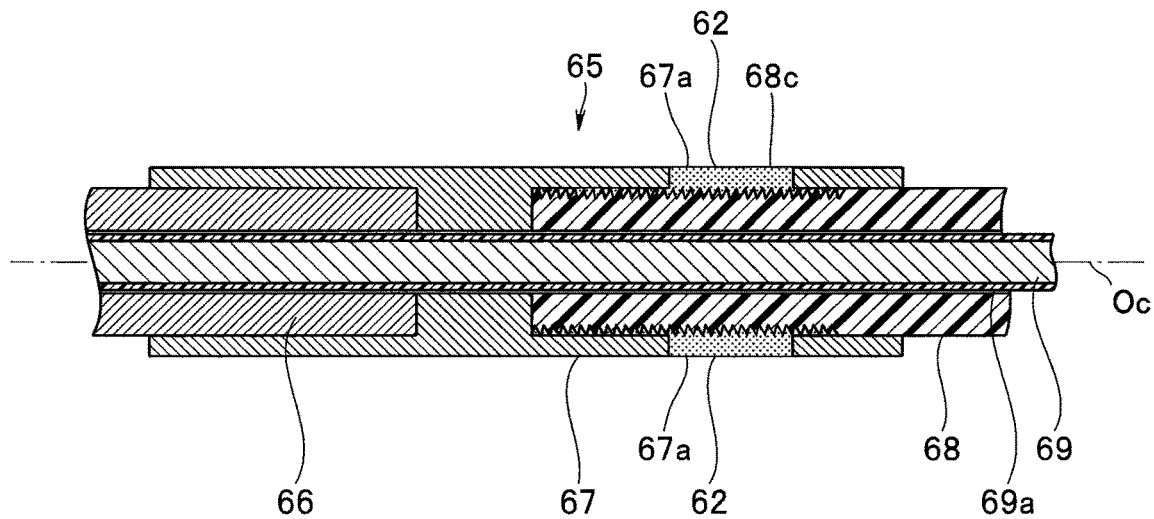
FIG. 15 is a main part cross-sectional view illustrating the connection structure of the distal end side of the wire guide tube and the coupling portion according to the third modification of the first embodiment.
Figure 16:
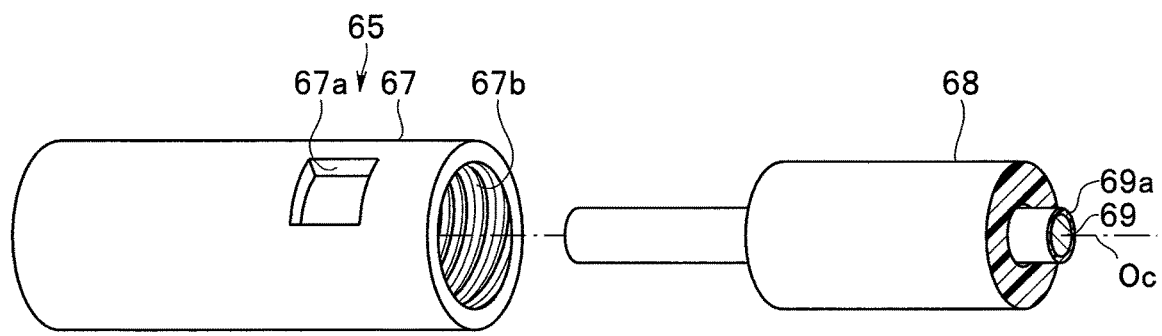
FIG. 16 is an exploded perspective view illustrating the wire guide tube and the coupling portion according to a fourth modification of the first embodiment.
Figure 17:
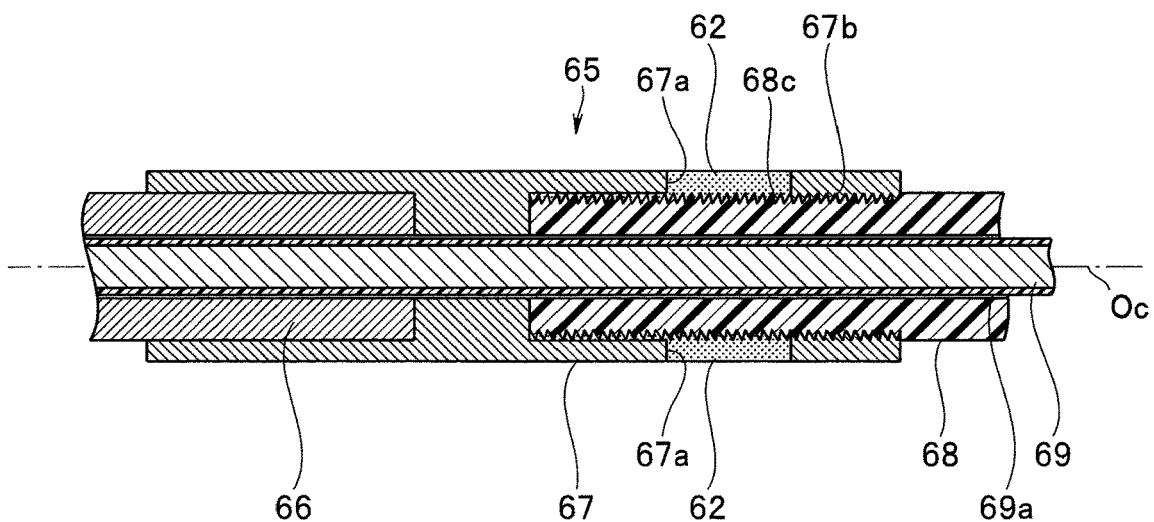
FIG. 17 is a main part cross-sectional view illustrating the connection structure of the distal end side of the wire guide tube and the coupling portion according to the fourth modification of the first embodiment.

Alternatively, in place of the concave portion 68a obtained by cutting out part of the outer peripheral portion of the wire guide tube 68 into a flat plate shape, a concave portion 68c having a screw shape may be formed by cutting out part of the outer peripheral portion of the wire guide tube 68 into a helical shape about the central axis Oc as illustrated in, for example, FIGS. 14 and 15.

With this configuration, it is easy to fabricate the concave portion 68c and position the concave portion 68c with respect to the opening 67a of the second coupling member 67.

In this case, fabrication of the concave portion 68c having a helical shape may be performed by the tubular portion 67 by providing a female screw part 67b to the inner periphery of the second coupling member 67 as illustrated in, for example, FIGS. 14 and 15. Specifically, when the female screw part 67b having a diameter smaller than the outer diameter of the wire guide tube 68 is provided to the inner periphery of the second coupling member 67, it is possible to form the concave portion 68c at the outer periphery of the wire guide tube 68 by screwing and inserting the wire guide tube 68 into the second coupling member 67.

Figure 18:
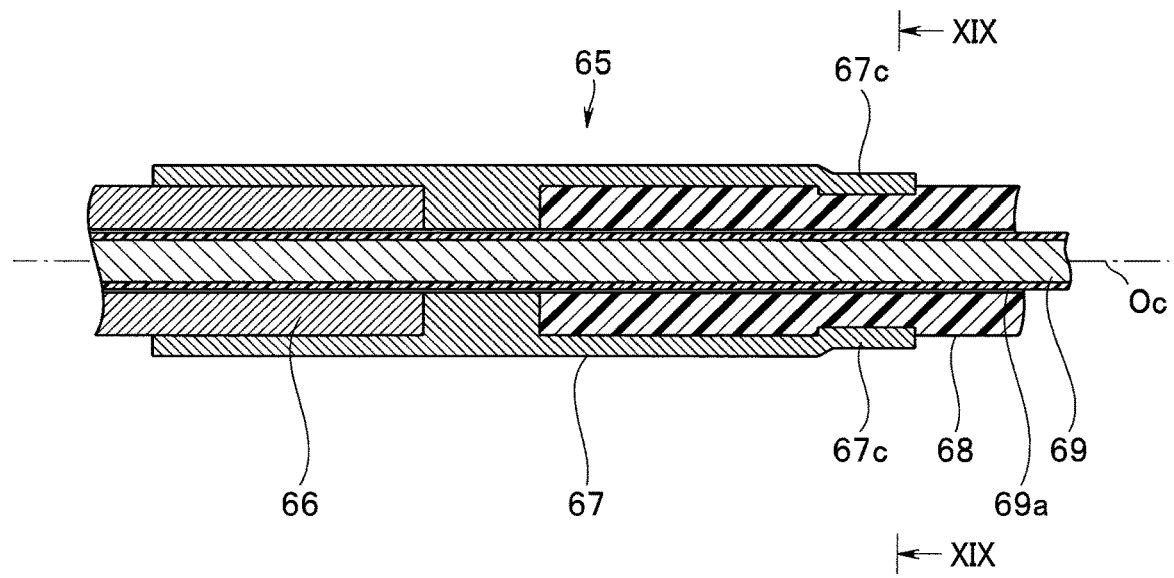
FIG. 18 is a main part cross-sectional view illustrating the connection structure of the distal end side of the wire guide tube and the coupling portion according to a second embodiment.
Figure 19:
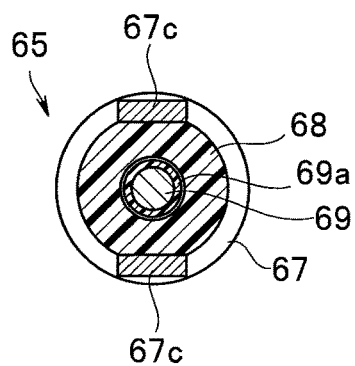
FIG. 19 is a cross-sectional view taken along line XIX-XIX in FIG. 18 according to the second embodiment.
Figure 20:
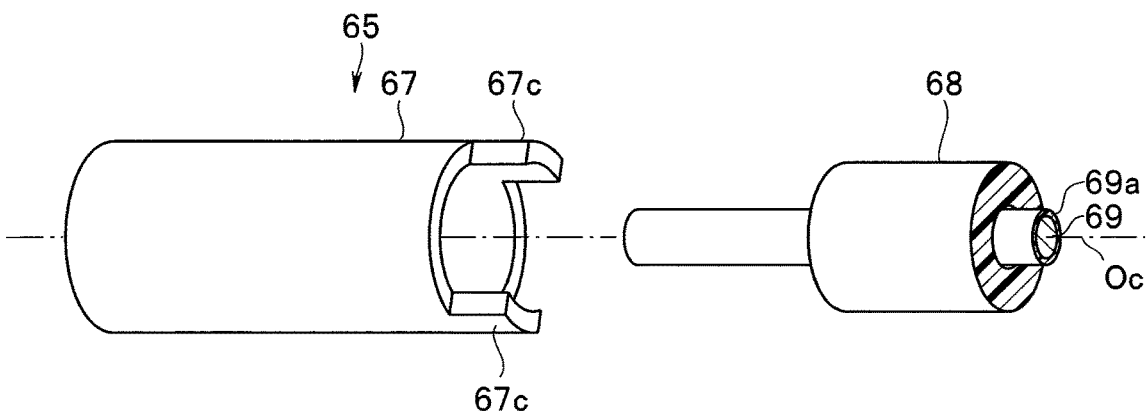
FIG. 20 is an exploded perspective view illustrating the wire guide tube and the coupling portion according to the second embodiment.
Figure 21:
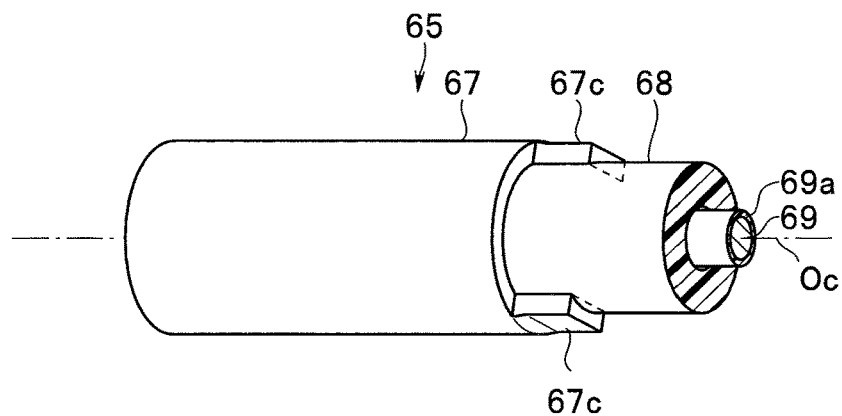
FIG. 21 is a perspective view illustrating the wire guide tube connected with the coupling portion according to the second embodiment.
Figure 22:
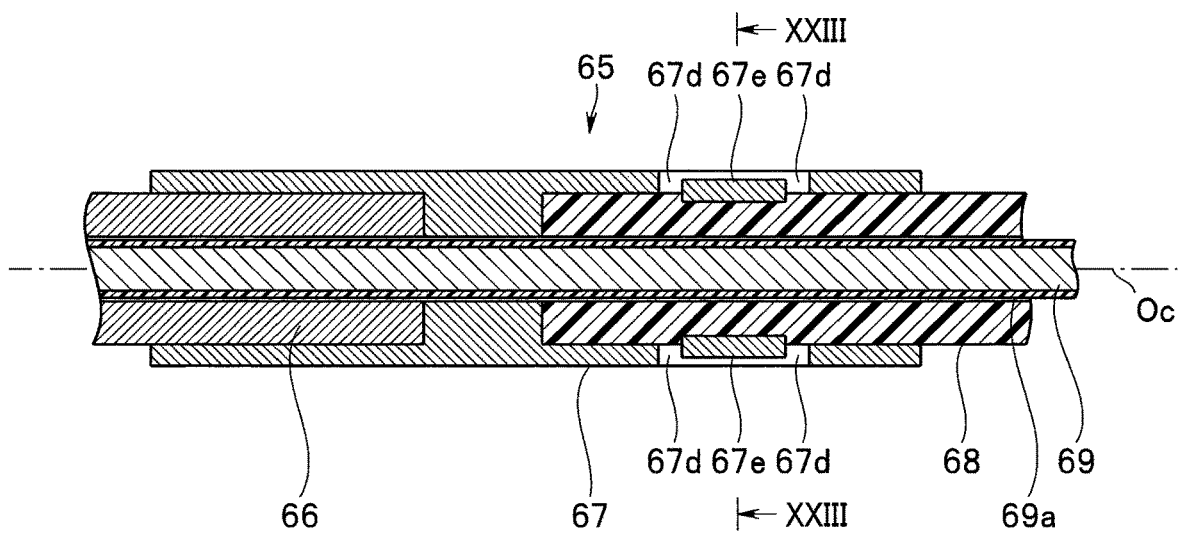
FIG. 22 is a main part cross-sectional view illustrating the connection structure of the distal end side of the wire guide tube and the coupling portion according to a first modification of the second embodiment.
Figure 23:
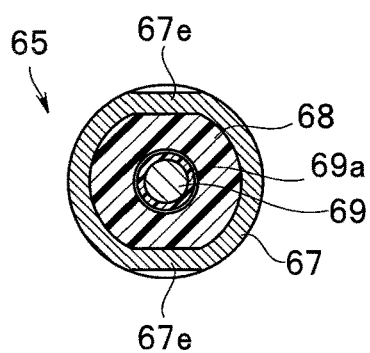
FIG. 23 is a cross-sectional view taken along line XXIII-XXIII in FIG. 22 according to the first modification of the second embodiment.
Figure 24:
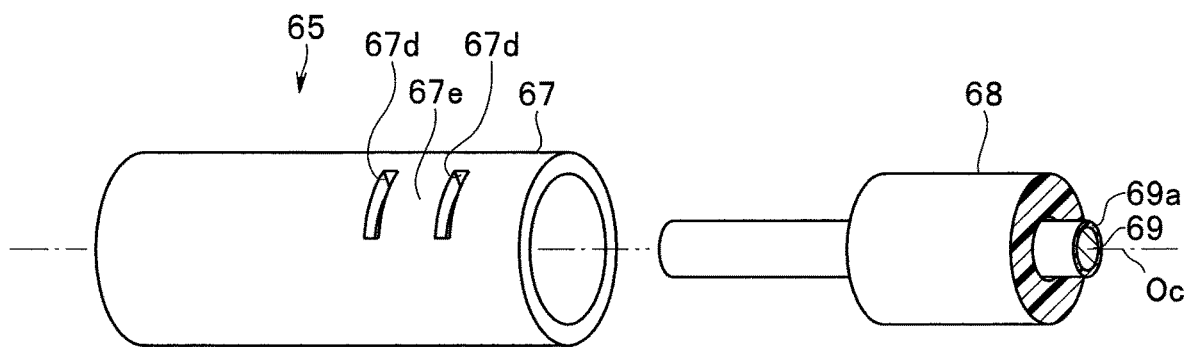
FIG. 24 is an exploded perspective view illustrating the wire guide tube and the coupling portion according to the first modification of the second embodiment.
Figure 25:
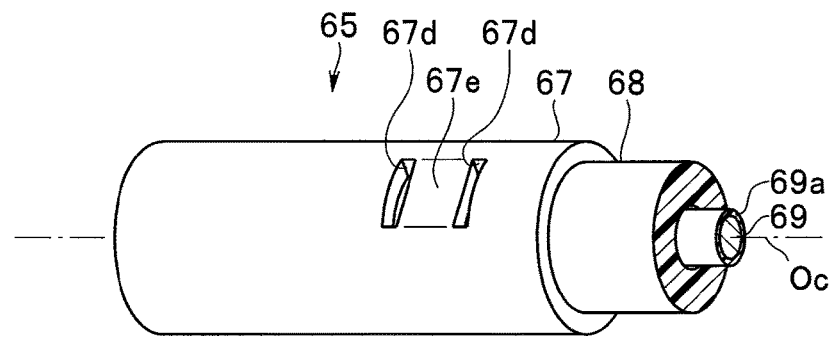
FIG. 25 is a perspective view illustrating the wire guide tube connected with the coupling portion according to the first modification of the second embodiment.

FIGS. 18 to 21 relate to a second embodiment of the present invention: FIG. 18 is a main part cross-sectional view illustrating the connection structure of the distal end side of the wire guide tube and the coupling portion; FIG. 19 is a cross-sectional view taken along line XIX-XIX in FIG. 18; FIG. 20 is an exploded perspective view illustrating the wire guide tube and the coupling portion; and FIG. 21 is a perspective view illustrating the wire guide tube connected with the coupling portion. Note that although the above-described embodiment has a configuration in which the second coupling member 67 and the wire guide tube 68 are connected with each other by bonding using the bonding agent 62, the present embodiment is mainly different in that the second coupling member 67 and the wire guide tube 68 are connected with each other by swaging. Any other component same as that of the above-described first embodiment is denoted by the same reference sign as appropriate and description thereof is omitted.

As illustrated in FIGS. 18 to 21, a pair of plastic deformation portions 67c are integrally formed at the second coupling member 67 of the coupling portion 65. The plastic deformation portions 67c are each configured as a protrusion piece having a tongue piece shape and protruding from an end part of the second coupling member 67 in the direction of the central axis Oc, and are disposed at positions rotationally symmetric to each other with respect to the central axis Oc.

The plastic deformation portions 67c are plastically deformed in the inward radial direction of the second coupling member 67 after the wire guide tube 68 is inserted into the second coupling member 67. Accordingly, part of the outer periphery of the wire guide tube 68 is swaged and fixed by the plastic deformation portions 67c.

Such an embodiment can achieve effects substantially the same as those of the above-described first embodiment.

As illustrated in, for example, FIGS. 22 to 25, a plurality (for example, two) of pairs of slits 67d in the circumferential direction may be provided to the wall portion of the second coupling member 67 by lasering or the like, and a plastic deformation portion 67e may be formed between the slits 67d of each pair.

Note that the present invention is not limited to the above-described embodiments but may be provided with modifications and changes in various kinds of manners, which are included in the technical scope of the present invention. For example, although the embodiments describe above an example in which the driven body driven by the operation wire is the movement lens frame, the present invention is not limited thereto but the driven body may be, for example, a raising base (forceps elevator). Components of the above-described embodiments and modifications may be combined as appropriate.

What is claimed is:
1. An insertion instrument comprising:
a wire having one end part fixed to a driven body and configured to transfer drive power from a drive source to the driven body;
a tube that is consecutively formed of polyetheretherketone from one end side to another end side and into which the wire is inserted;
a first coupling member fixed to an objective unit in which the driven body is incorporated;
a second coupling member fixed to the first coupling member, the second coupling member including a tubular portion into which an end part of the tube is inserted, the second coupling member being configured to couple the tube;
an opening penetrating in a radial direction at part of a wall portion of the second coupling member;
a concave portion formed at an outer peripheral surface of the tube so as to correspond to the opening; and
a bonding agent integrally filling the opening and the concave portion.

2. The insertion instrument according to claim 1, wherein the concave portion is formed by cutting out part of an outer peripheral portion of the tube into a flat plate shape having a predetermined width in a direction orthogonal to a central axis direction of the tube.

3. The insertion instrument according to claim 1, wherein the concave portion is formed by cutting out part of an outer peripheral portion of the tube about a central axis of the tube.

4. The insertion instrument according to claim 1, wherein the wire includes a layer made of polytetrafluoroethylene on a surface of the wire.

5. The insertion instrument according to claim 1, wherein the tube includes a layer made of polytetrafluoroethylene on an inner surface of the tube.

6. An insertion instrument comprising:
a wire having one end part fixed to a driven body and configured to transfer drive power from a drive source to the driven body;
a tube that is consecutively formed of polyetheretherketone from one end side to another end side and into which the wire is inserted;
a first coupling member fixed to an objective unit in which the driven body is incorporated;
a second coupling member fixed to the first coupling member, the second coupling member including a tubular portion into which an end part of the tube is inserted, the second coupling member being configured to couple the tube; and a plastic deformation portion provided to the second coupling member, wherein the end part of the tube is fixed by swaging that plastically deforms the plastic deformation portion inward in a radial direction of the second coupling member.

7. The insertion instrument according to claim 6, wherein the plastic deformation portion is a protrusion piece protruding in a central axis direction from the second coupling member.

8. The insertion instrument according to claim 6, wherein the plastic deformation portion is formed between slits provided in a pair in a circumferential direction at a wall portion of the second coupling member.

9. The insertion instrument according to claim 6, wherein the wire includes a layer made of polytetrafluoroethylene on a surface of the wire.

10. The insertion instrument according to claim 6, wherein the tube includes a layer made of polytetrafluoroethylene on an inner surface of the tube.

* * * * *